United States Patent
Hu et al.

(10) Patent No.: US 9,380,928 B2
(45) Date of Patent: Jul. 5, 2016

(54) STRUCTURE OF IMAGING PART IN ELECTRONIC VISUALIZED CATHETER

(75) Inventors: Wei-Zhi Hu, Sakura (JP); Takeshi Segi, Sakura (JP); Kenichi Nakatate, Sakura (JP); Katsuya Yamagami, Sakura (JP)

(73) Assignee: FUJIKURA LTD., Tokyo (JP)

( * ) Notice: Subject to any disclaimer, the term of this patent is extended or adjusted under 35 U.S.C. 154(b) by 0 days.

(21) Appl. No.: 13/485,109

(22) Filed: May 31, 2012

(65) Prior Publication Data

US 2012/0310043 A1  Dec. 6, 2012

Related U.S. Application Data

(60) Provisional application No. 61/493,558, filed on Jun. 6, 2011.

(51) Int. Cl.
  *A61B 1/00* (2006.01)
  *A61B 1/05* (2006.01)
  *G02B 23/24* (2006.01)
  *A61B 1/015* (2006.01)
  *H04N 5/225* (2006.01)

(52) U.S. Cl.
  CPC ........... *A61B 1/00018* (2013.01); *A61B 1/0011* (2013.01); *A61B 1/00096* (2013.01); *A61B 1/051* (2013.01); *G02B 23/2423* (2013.01); *G02B 23/2484* (2013.01); *A61B 1/015* (2013.01); *H04N 5/2253* (2013.01); *H04N 5/2254* (2013.01); *H04N 2005/2255* (2013.01)

(58) Field of Classification Search
  USPC ................................. 600/109, 110; 257/432
  See application file for complete search history.

(56) References Cited

U.S. PATENT DOCUMENTS

| 5,220,198 | A | 6/1993 | Tsuji |
| 5,797,837 | A | 8/1998 | Minami |
| 6,142,930 | A | 11/2000 | Ito et al. |
| 7,591,780 | B2 * | 9/2009 | Jacobsen ................. A61B 1/05 257/432 |
| 7,773,122 | B2 * | 8/2010 | Irion et al. .................... 600/109 |
| 2005/0043586 | A1 | 2/2005 | Suzushima |
| 2009/0185032 | A1 | 7/2009 | Sakai et al. |
| 2009/0225157 | A1 | 9/2009 | Orihara et al. |
| 2011/0118549 | A1 | 5/2011 | Han |
| 2011/0137117 | A1 * | 6/2011 | Jacobsen et al. .............. 600/109 |

FOREIGN PATENT DOCUMENTS

| CN | 101461702 A | 6/2009 |
| CN | 101526654 A | 9/2009 |

(Continued)

OTHER PUBLICATIONS

International Search Report dated Jul. 31, 2012 issued in counterpart application PCT/JP2012/064312.
Communication dated Sep. 2, 2014, issued by the Japanese Patent Office in counterpart Japanese application No. 2013-519475.
Communication dated Oct. 31, 2014, issued by the European Patent Office in counterpart European application No. 12797311.3.
Machine Translation of JP 09-102896.
Machine Translation of JP 2001-037713.

(Continued)

*Primary Examiner* — John P Leubecker
*Assistant Examiner* — Rajaa El Alami
(74) *Attorney, Agent, or Firm* — Sughrue Mion, PLLC

(57) ABSTRACT

An imaging part of an electronic visualized catheter including, an object lens system, and a solid state imaging element which is positioned to receive light output from the object lens system and which photoelectrically converts the light output from the object lens system into an electric signal, wherein an output lens face of the object lens system is planar, and the output lens face is joined to a light receiving surface of the solid state imaging element.

4 Claims, 8 Drawing Sheets

(56) References Cited

FOREIGN PATENT DOCUMENTS

| | | | |
|---|---|---|---|
| CN | 102058379 | A | 5/2011 |
| JP | 04-218136 | A | 8/1992 |
| JP | 09-102896 | A | 4/1997 |
| JP | 2001-037713 | A | 2/2001 |
| JP | 2001-136421 | A | 5/2001 |
| JP | 2002-095626 | A | 4/2002 |
| JP | 2006-034458 | A | 2/2006 |
| JP | 2008-253451 | A | 10/2008 |
| JP | 2009-240518 | A | 10/2009 |
| WO | 03081831 | A2 | 10/2003 |
| WO | 2004082470 | A1 | 9/2004 |

OTHER PUBLICATIONS

Machine Translation of JP 2008-253451.
Machine Translation of JP 2006-034458.
Machine Translation of JP 2009-240518.
Machine Translation of JP 2001-136421.
Machine Translation of JP 2002-095626.
Communication dated Mar. 18, 2015 from the State Intellectual Property Office of People's Republic of China in counterpart Application No. 201280025729.3.
Communication dated Nov. 17, 2015 from the Japanese Patent Office in counterpart application No. 2013519475.

* cited by examiner

US 9,380,928 B2

STRUCTURE OF IMAGING PART IN ELECTRONIC VISUALIZED CATHETER

CROSS-REFERENCE TO RELATED APPLICATION

This application is a non-provisional application claiming priority to and the benefit of U.S. provisional application No. 61/493,558, filed Jun. 6, 2011. The entire contents of which are incorporated herein by reference.

BACKGROUND OF THE INVENTION

1. Field of the Invention

Apparatuses consistent with exemplary embodiments relate to a catheter ("endoscope" or "visualized catheter") that has a mechanism for obtaining an image with the aim of providing an electronic visualized catheter using a solid state imaging element or confirming the insertion position, and in particular relates to the structure of an imaging part at the distal end of the insertion portion that is inserted into the interior of the observation object.

2. Description of Related Art

In order to observe the state of the interior of a body of a human or animal, or the interior of various machines and equipment, catheters are widely used. Catheters that are mainly used are those of a type involve inserting an image fiber in the interior of an observation object such as a living body and optically drawing out the image of the observation object region to the outside of the observation object to be observed (fiberscope type), and electronic ones that involve inserting a small solid state imaging element in the interior of an observation object, converting the image of the observation object region into an electric signal, drawing out that electric signal to the outside of the observation object, and observing the image with an external monitor.

As a solid state imaging element of the latter electronic visualized catheter, conventionally an image sensor having a CCD (charged coupled device) is often used, but recently an image sensor having a CMOS (complementary metal oxide semiconductor) has come to be used.

In a catheter that uses an image sensor including this type of solid state imaging element, the distal end portion that is inserted into the interior of an observation object, that is, the imaging part, is constituted to have, in addition to the solid state imaging element, an object lens system for forming an image of the observation object region on the light receiving surface of the solid state imaging element, and a circuit board (generally a printed circuit board) on which are formed conductor wiring layers such as an input signal line to the solid state imaging element, an output signal from the solid state imaging element, and a power potential line to the solid state imaging element.

Conventionally, as prior art documents of catheters that use an image sensor including this type of solid state imaging element, in particular, prior art documents relating to the structure of an imaging part, for example there are Japanese Unexamined Patent Application, First Publication No. H09-102896 (Patent Document 1) and Japanese Unexamined Patent Application, First Publication No. H04-218136 (Patent Document 2).

Patent Document 1 discloses a structure of the distal end portion of a catheter that uses a CCD image sensor as an imaging element, that is to say, the imaging part. FIG. 4 of Patent Document 1 discloses a structure in which, as the imaging part of the catheter, a lens barrel that houses the object lens is arranged on the front surface side (the side that should be made to face the observation object region) of a circuit board that has an opening hole, and a solid state imaging element is disposed on the back surface side of the circuit board (the surface on the opposite side with respect to the object lens system). In this structure, the outgoing light from the object lens system passes through the opening hole that is formed in the circuit board, and reaches the light receiving surface of the solid state imaging element.

In Patent Document 2, FIG. 3 and the like show a structure in which the circuit board is folded so as to form a U-shape, a solid state imaging element including a CCD image sensor is mounted on the outer side of the front surface thereof (corresponding to the bottom of the U shape), and an object lens system is disposed at a position separated from the light receiving surface of the solid state imaging element.

In the prior art mentioned above, since the object lens system is separated (placed at a distance) with respect to the light receiving face of the solid state imaging element, the image distance of the object lens system unavoidably increases. This means that, in order to obtain a wider angle of view, a lens of a glass material with a high refractive index, a small radius of curvature or a small diameter, and a concave surface is required, and means that the lens structure and processing become complex. Generally, in an endoscope or visualized catheter, a short object distance and a large angle of view are desired in order to observe the observation target region, particularly in a narrow lumen.

Also, since the object lens system is arranged separate with respect to the light receiving surface of the solid state imaging element, surrounding debris, bodily fluids and the like easily infiltrate the gap between the object lens system and light receiving surface of the solid state imaging element, and so there is a risk of these infiltrates exerting a bad influence during the observation.

SUMMARY

Exemplary embodiments described herein were developed with the aforementioned circumstances as a background, and an object is to provide an imaging part of an electronic visualized catheter that is capable of easily increasing the angle of view, and moreover hinders the ingress of surrounding debris and fluids such as bodily fluids into the space between the object lens system and the light receiving surface of the solid state imaging element.

According to an aspect of an exemplary embodiment, an imaging part of an electronic visualized catheter includes an object lens system, and a solid state imaging element which is positioned to receive light output from the object lens system and which photoelectrically converts the light output from the object lens system into an electric signal. An output lens face of the object lens system is planar, and the output lens face is joined to the light receiving surface of the solid state imaging element.

In the structure of the imaging part of such an electronic visualized catheter, since the emission-side lens surface of the object lens system is joined to the light receiving surface of the solid state imaging element by the surfaces themselves, the distance between the object lens system and the light receiving surface is effectively zero, and for that reason the angle of view of the object lens system increases, and observing an observation object region with a field of view of a wide range easily becomes possible.

Moreover, since a gap does not exist between the objective lens system and the light receiving surface, there is little risk of debris, bodily fluids or the like ingressing between the object lens system and the light receiving surface, and thereby exerting an adverse effect on image observation of the observation object region.

Also, in the structure of the imaging part of the electronic visualized catheter of one or more exemplary embodiments, the imaging part further includes a flexible printed wiring board, and a sleeve with a hollow tubular shape including a distal end portion which is open. The flexible printed wiring board includes a bottom plate portion, and a first side wall plate portion and a second sidewall plate portion, in which the first and second sidewall plate portions are each continuous a side of the bottom plate portion, and each extends from the bottom plate portion in the same direction away from the distal end portion. The bottom plate portion includes an opening that penetrates a plate surface of the bottom plate portion. The solid state imaging element is disposed on a surface of the bottom plate portion away from the distal end portion, and the light receiving surface of the solid state imaging element faces the distal end portion, and is exposed through the opening in the bottom plate portion. The output lens face is disposed within the opening portion. The object lens system, the solid state imaging element, and the flexible printed wiring plate are disposed within the sleeve such that an incident lens face, opposite the output lens face, is positioned at the distal end portion of the sleeve.

Here, it is possible to express the bent shape achieved by the pair of side wall plate portions and the bottom plate portion as "nearly a U-shape" in which the bottom plate portion corresponds to the bottom portion of the U-shape. "Nearly a U-shape" does not mean a shape of a U in the strict sense, that is to say, a curved shape, and includes a shape in which the bent portions of the U shape are bent perpendicularly. Therefore, with regard to the bent shape of this flexible printed wiring board, "nearly a U-shape" is stated in the present specification.

In this structure, by bringing object lens system close to the light receiving surface of the solid state imaging element that is mounted on the flexible printed wiring board, it is possible to make a structure in which the lens face of the emission side of the object lens system and the light receiving surface make contact by their surfaces.

Also, a lens with a small diameter may be applied, provided the smallest diameter of the lens is large enough to be able to cover an image sensor area of the light receiving surface of the solid state imaging element.

Also, in the structure of the imaging part in an electronic visualized catheter of one or more exemplary embodiments, each of the first and second side wall plate extends in a length direction from the bottom plate portion, and the length direction is parallel to an axial direction of the sleeve. Moreover, the flexible printed wiring board includes a plurality of conductor wiring layers, in which the plurality of conductor wiring layers includes at least one conductor wiring layer which is electrically connected to a terminal portion of the solid state imaging element and extends along the first side wall plate portion. The plurality of conductor wiring layers further includes at least one conductor wiring layer which extends along the second side wall plate portion.

In this structure, the conductor wiring layers are formed on only one surface among the two surfaces of the flexible printed wiring board, and moreover the solid state imaging element is also mounted on the surface of the same side of the flexible printed wiring board. Accordingly, among the two surfaces of the flexible printed wiring board, it is possible to utilize one surface only, and in that case, compared with the case of using both surfaces of the flexible printed wiring board, the processing cost becomes lower, and so it is possible to achieve a cost reduction of a catheter.

DETAILED DESCRIPTION

Figure 1:
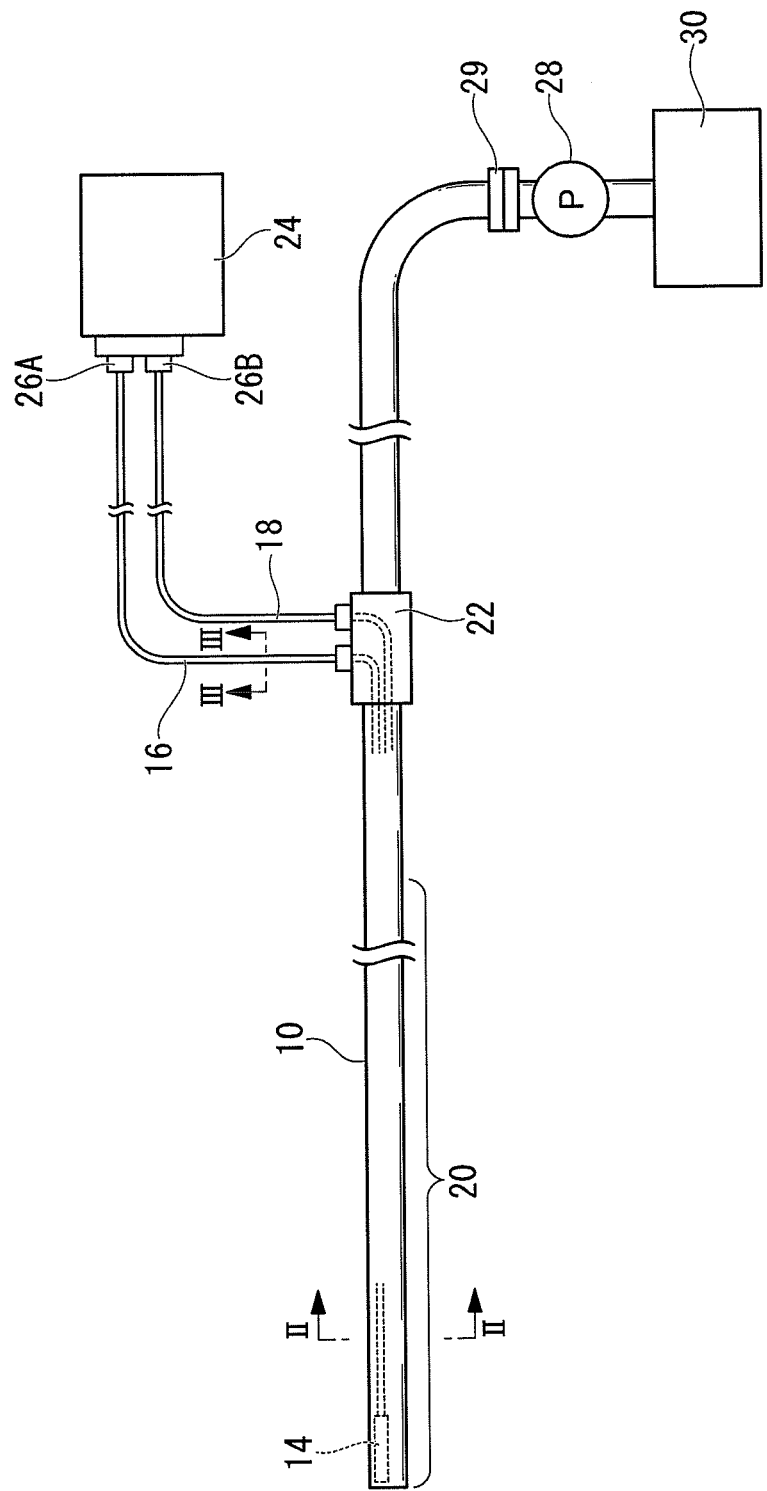
FIG. 1 is an outline view that shows one example of the overall electronic catheter of an exemplary embodiment.

Hereinbelow, exemplary embodiments are described in detail referring to the drawings.

FIG. 1 shows an exemplary embodiment that incorporates an electronic visualized catheter in a feeding tube for supplying a fluid or liquid such as a nutrition solution or medicine to the inside of a living body such as a human body.

Figure 2:
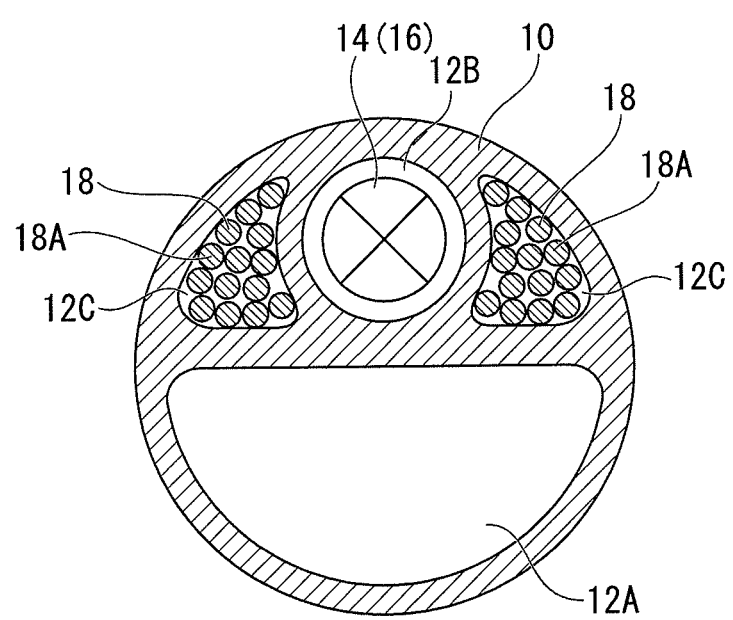
FIG. 2 is a close-up cross-sectional view along line II-II of FIG. 1.

In FIG. 1, a feeding tube 10 is made with flexible resin, such as silicon and polyurethane, and the distal end portion corresponds to an insertion portion 20 that is inserted in the inside of an observation object, such as a human body. FIG. 2 shows the cross-sectional structure of the feeding tube 10.

As shown in FIG. 2, one or more of a first hollow passage 12A for passing a nutrition solution or medication, a second hollow passage 12B in which an imaging part 14 of a catheter (or a portion of an electrical cable 16 that is consecutive therewith) is inserted and adhesively fixed, and one or more (two shown in the illustrated example) of a third hollow passage 12C in which a light guide 18 including a plurality of optical fibers 18A for brightly illuminating the observation object region is inserted and adhesively fixed, are formed along the lengthwise direction within the feeding tube 10.

The distal end of the first hollow passage 12A is opened at the distal end of the feeding tube 10 or the vicinity thereof. Moreover, the rear end side of the feeding tube 10 is connected with a supply tub 30 that contains a nutrition solution, medicine or the like, through a connector 29 and a pump 28.

The imaging part 14 is arranged at the distal end portion (insertion portion 20) of the feeding tube 10. The electric cable 16 that is consecutive with the rear end of the imaging part 14 is branched off from the feeding tube 10 at a branch portion 22 to be pulled out to the outside, and is electrically connected in a detachable manner to an external device 24 that includes a signal processing portion, and operation portion, a power supply portion, an image display portion, a light source portion and the like via a connector 26A.

A light guide 18 is led from the distal end to the rear of the feeding tube 10, is branched off from the feeding tube 10 at the branch portion 22 to be pulled out to the outside, and is optically connected to the light source portion of the external device 24 through connector 26B.

Here, also the signal processing portion, operation portion, power supply portion, and the image display portion and light source portion are referred to collectively as the external device 24, these portions may of course be suitably separated as required.

Figure 3:
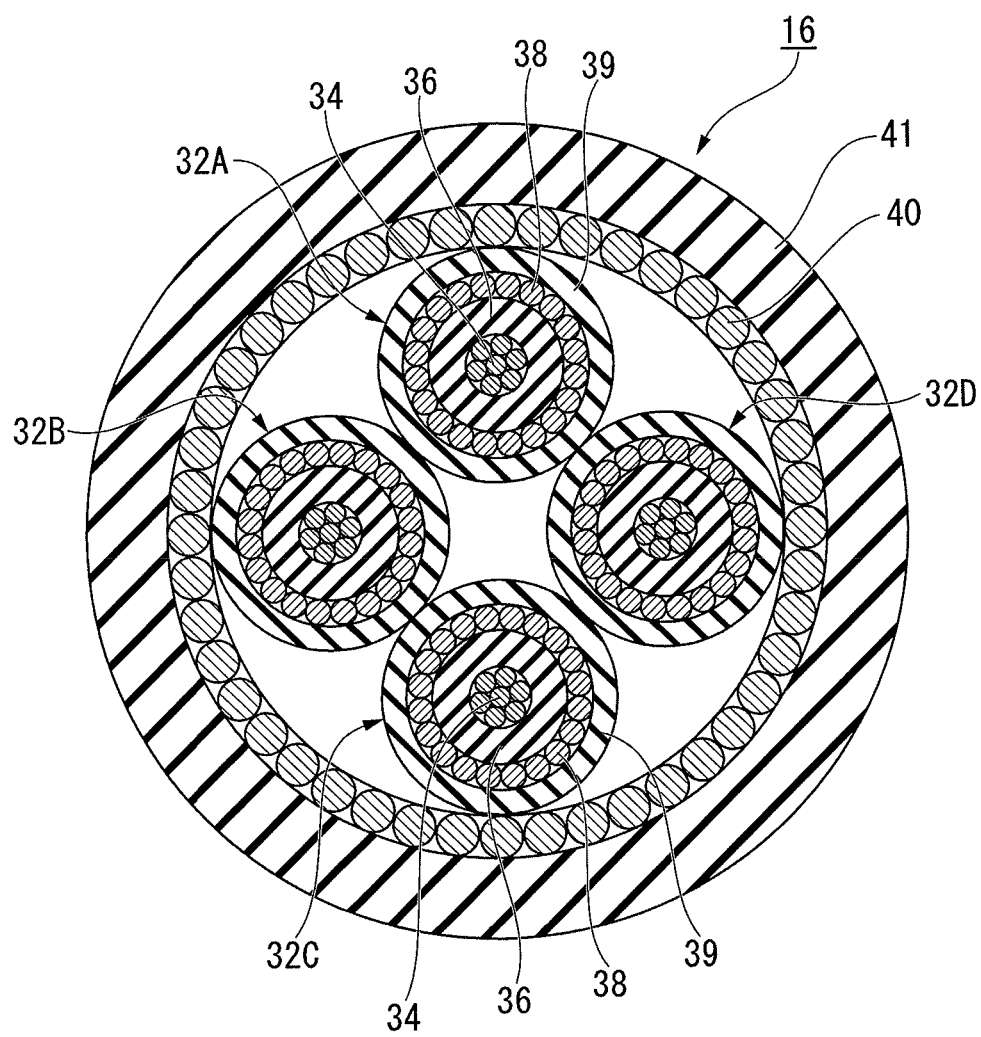
FIG. 3 is a close-up cross-sectional view along line III-III of FIG. 1, that is to say, a close-up cross-sectional view of the gathered cable.

The electric cable 16, in addition to transmitting input signals to a solid state imaging element, and output signals from the solid state imaging element, also serves to impart a power supply potential and a ground potential to the solid state imaging element, and for example as shown in FIG. 3, is constituted by a four-core gathered coaxial cable that is formed by gathering four coaxial cables 32A, 32B, 32C, 32D. Each coaxial cable 32A, 32B, 32C, 32D respectively is constituted by a central conductor 34, an inner insulating layer 36 that encloses the central conductor 34, an outer conductor 38 that encloses the inner insulating layer 36, and an outer insulating layer (sheath) 39 that includes the outer conductor 38. The entire collection of the four coaxial cables 32A, 32B, 32C, 32D is enclosed by a ground conductor layer (shield layer) 40, and moreover that ground conductor layer 40 is enclosed by a protective covering layer (jacket) 41.

In the device shown in FIG. 1, for the observation object region inside an observation object, such as a human body, simultaneously with performing observation while radiating light by the light guide 18, it is possible to supply a nutrition solution, medicine, and the like to the inside of the human body.

Instead of the light guide 18, a cable with a light emitting element such as a light emitting diode attached to the distal end may be inserted into the third hollow passage 12C, and light may be irradiated on the observation object region by the light emitting element. Also, the first hollow passage 12A may be used as a discharge passage for sucking and discharging bodily fluids from inside the human body, instead of being used as a supply passage for a nutrition solution, medicine and the like, and in that case a discharge liquid storage tub may be provided instead of the supply tub 30. Moreover, the first hollow passage 12A can also be used in order to pass a tiny surgical instrument. Also, the first hollow passage 12A may be omitted. Furthermore, the light guide 18 may be passed through the hollow passage that passes the imaging part 14 and the cable 16 together therewith, and in that case, it is possible to omit one among the second hollow passage 12B and the third hollow passage 12C.

Figure 4:
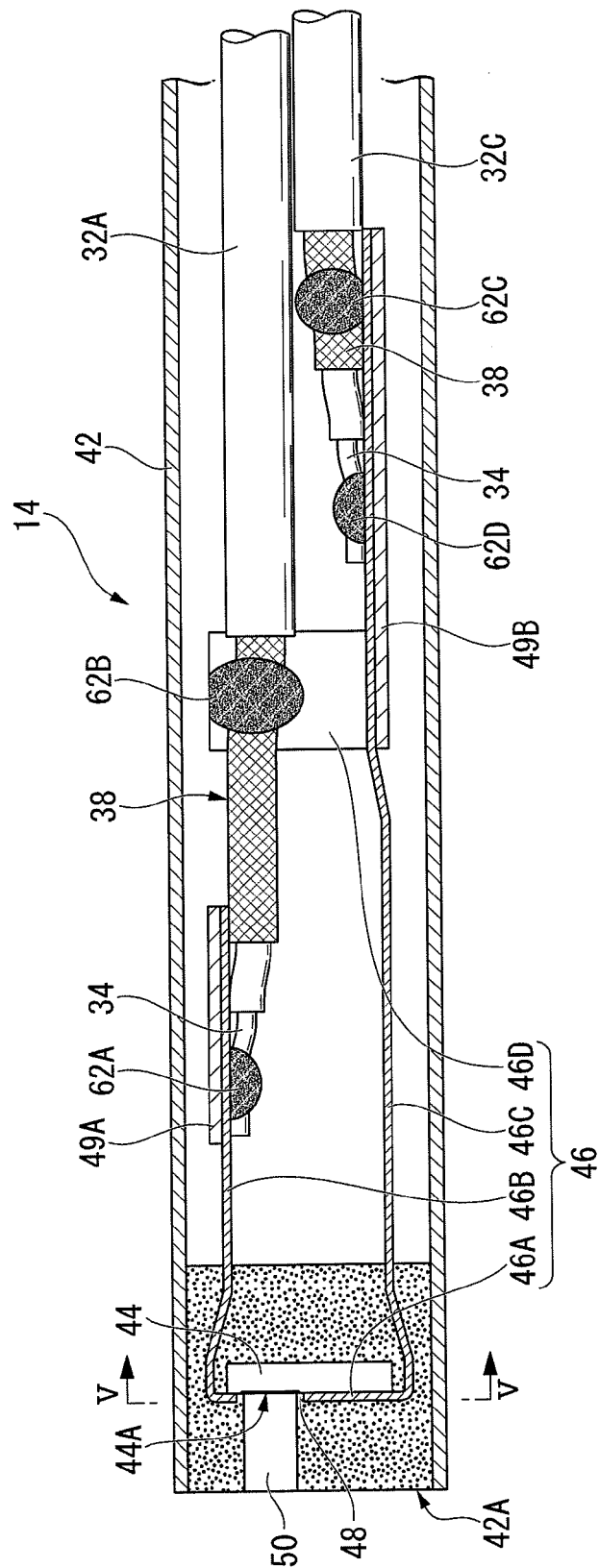
FIG. 4 is a close-up longitudinal side view of one example of the imaging part of the electronic visualized catheter of an exemplary embodiment.
Figure 5:
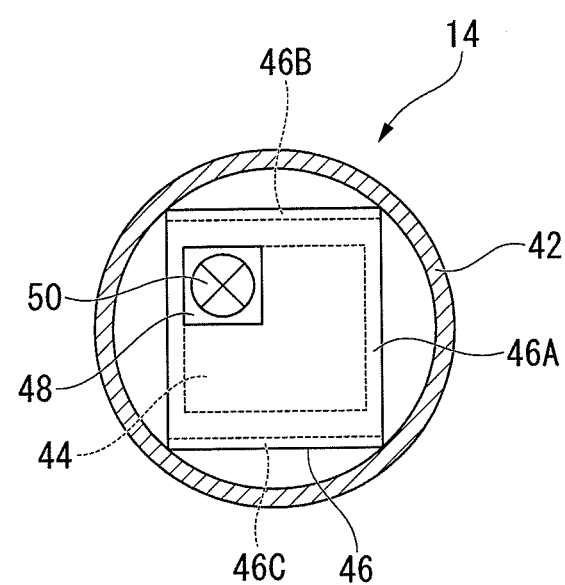
FIG. 5 is a close-up cross-sectional view along line V-V of FIG. 4.
Figure 6:
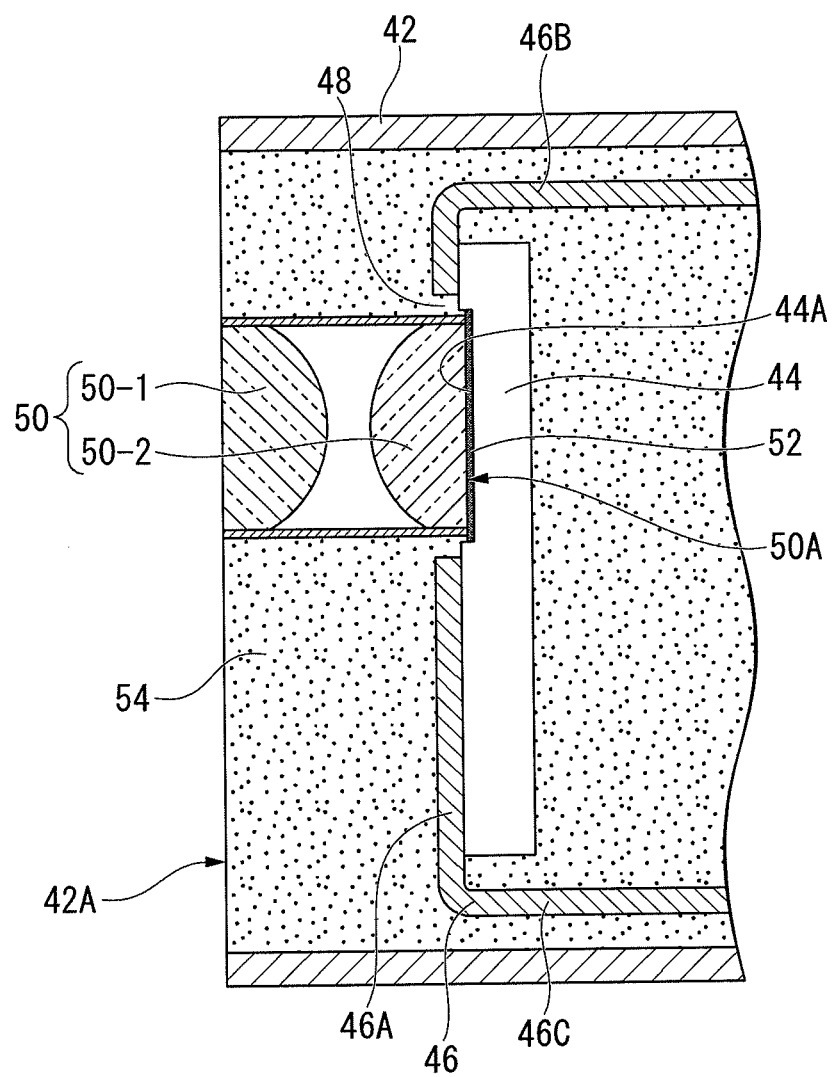
FIG. 6 is a close-up longitudinal side view that shows in further close-up the distal end portion of the imaging part that is shown in FIG. 4.

FIG. 4 to FIG. 6 show the structure of the imaging part 14 in the catheter.

In the imaging part 14, a circuit board 46 with a solid state imaging element (semiconductor chip) 44, for example, a CMOS image sensor mounted thereon, and an object lens system 50 are housed on the inside of a hollow tubular sleeve 42 that is formed by a rigid material such as stainless steel or the like.

In the sleeve 42, an opening 42A is formed at least one distal end in the axial direction thereof (the region that corresponds to the distal end of the insertion portion 20).

The circuit board 46 is constituted by a flexible printed circuit board (FPC) that uses a flexible material such as a polyimide resin as an insulating substrate, and is formed in a bent shape so that the overall cross-section thereof has nearly a U-shape. In greater detail, the circuit board 46 has a rectangular plate-shaped bottom plate portion 46A, and a pair of rectangular side wall plate portions 46B and 46C that are consecutive with both sides of the bottom plate portion 46A.

On side wall plate portion 46B stands up nearly perpendicularly from one end side portion of the bottom portion 46A, and the other side wall plate portion 46C stands up nearly perpendicularly from the other end side portion of the bottom plate portion 46A that is perpendicular with the end side portion, such that the pair of side wall plate portions 46A and 46C extend in the same direction from the bottom plate portion 46A, and thereby the circuit board 46 is made in nearly a U-shape overall. Then, the circuit board 46 is placed so that the bottom plate portion 46A is perpendicular with respect to the center axial line of the sleeve 42, and moreover the side wall plate portions 46B and 46C are nearly parallel with the center axial line of the sleeve 42. A projection side portion 46D that projects laterally is continuously formed in an integral manner from the vicinity of the lengthwise intermediate position of the side wall plate portion 46C.

The bottom plate portion 46A of the circuit board 46 faces the distal end opening portion 42A of the sleeve 42, and the side wall plate portions 46B and 46C extend toward the rear of the sleeve 42. In the bottom plate portion 46A, an opening portion 48 that penetrates in the plate thickness direction thereof is formed. In the back face side of the bottom plate portion 46A (the side corresponding to the inside of the U shape), the solid state imaging element (semiconductor chip) 44, for example, a CMOS image sensor, is disposed. The solid state imaging element 44 is disposed so that the light receiving surface 44A thereof faces the distal end opening portion 42A of the of the sleeve 42, and the light receiving surface 44A faces the opening portion 48 of the of the circuit board 46. The opening portion 48 may be cut out of the plate surface of the circuit board 46 in the manner of a window as illustrated, or may be cut into the circuit board 46 from the sides thereof.

The object lens system 50, which is constituted so that the outgoing side lens face 50A is planar, is disposed in the distal end opening portion 42A of the sleeve 42. The object lens system 50 shown in FIG. 6 is constituted, from the incoming side, by the two lenses of a plano-convex lens 50-1 and a plano-convex lens 50-2, but the structure of the lens group of the object lens system 50 is of course not limited to the example of FIG. 6, provided it is constituted to cause the image of the observation object region to be formed on the light receiving surface 44A of the solid state imaging element 44, and moreover the outgoing side lens face 50A is planar.

In the object lens system 50, the portion of the emission side thereof is positioned within the opening portion 48 of the circuit board 46, and the planar lens face 50A is joined to the light receiving surface 44A of the solid state imaging element 44 so that the surfaces make contact. A transparent adhesive 52 such as an epoxy adhesive or an acrylic adhesive is used for the joining of the lens face 50A and the light receiving surface 44A. A non-transparent resin 54 such as a non-transparent adhesive with a black color, for example an epoxy resin or a silicon resin, or an urethane resin in which a black pigment such as carbon or the like has been mixed, is filled in the inside of the distal end portion of the sleeve 42, especially at a location that encloses the solid state imaging element 44.

Figure 7:
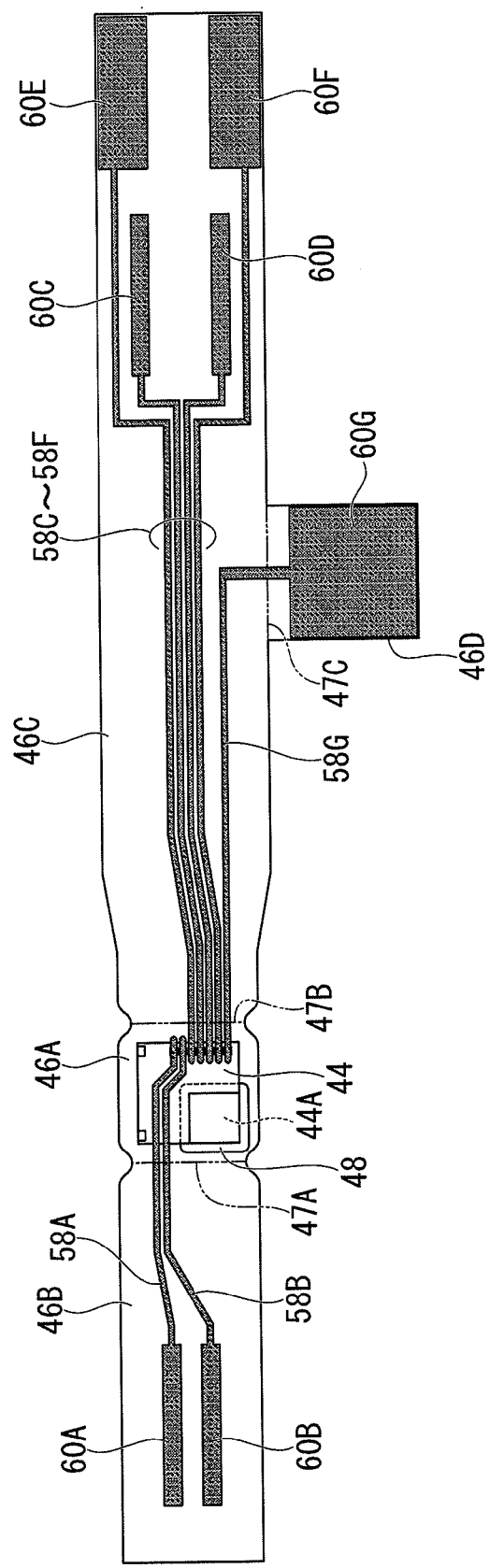
FIG. 7 is an expanded plan view that shows the circuit board, which is used in the imaging part shown in FIG. 4, expanded in a planar shape with the solid state imaging element mounted thereon.
Figure 8:
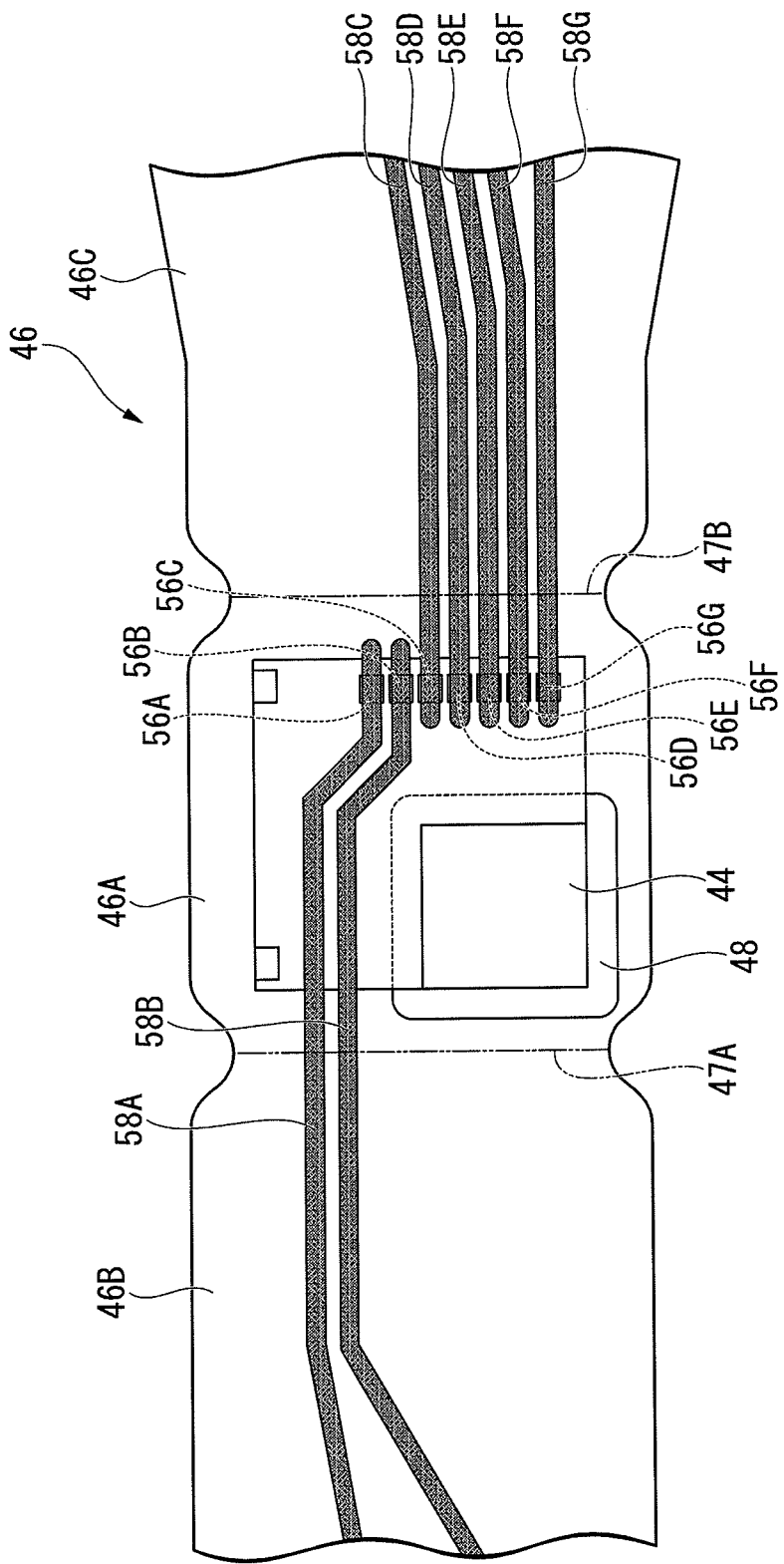
FIG. 8 is a close-up expanded plan view that enlarges portions of FIG. 7, in particular the portions mounted on the solid state imaging element.

FIG. 7 shows the appearance of the circuit board 46 that including FPC being expanded in a planar manner (the appearance of a planar state of not being bent in nearly a U shape), and moreover FIG. 8 shows the essential portions thereof (mainly the solid state imaging element mounted portions) in close-up. These FIG. 7 and FIG. 8 show on the facing side the surface of the side that becomes the inner side of the U-shape when the circuit board 46 is bent in nearly a U-shape. In FIG. 7 and FIG. 8, the two-dot chain lines 47A and 47B indicate the bending positions when bending the circuit board 46 in nearly a U-shape. Accordingly, the two-dot chain lines 47A and 47B correspond to the boundary positions of the bottom plate portion 46A and the side wall plate portions 46B and 46C. Also, a separate two-dot chain line 47C in FIG. 7 shows the bending position when folding back the projection side portion 46D with respect to the side wall plate portion 46C.

Referring to FIG. 4 to FIG. 8, the circuit board 46 including a FPC shall be described in greater detail.

A plurality of electrode pads 56A to 56G for the input signal, output signal and power supply potential of the solid state imaging element 44 are formed at the periphery of the solid state imaging element 44 that is mounted on the circuit board 46. The electrode pads 56A and 56B for example respectively serve to extract the positive output signal (positive analog signal: AOP) and the negative output signal (negative analog signal: AON). The electrode pads 56C and 56F for example respectively serve to impart a potential of 1.5 V from a low potential power supply (1.5 VDD) and a potential of 2.8 V from a high potential power supply (2.8 VDD) to the solid state imaging element 44, the electrode pads 56D and 56E respectively serve to impart a synchronization signal (HSYNC) and a clock signal (CLK) to the solid state imaging element 44, and the electrode pad 56G is one that serves to impart a ground potential (GND) to the solid state imaging element 44.

Conductor wiring layers 58A to 58G made with an electrically conductive material such as copper are formed on the circuit board 46, and one end of each of these conductor wiring layers 58A to 58G is electrically connected to the electrode pads 56A to 56G of the solid state imaging element 44. The conductor wiring layers 58A and 58B are extended from the bottom plate portion 46A to the one side wall plate portion 46B, with terminal electrodes 60A and 60B formed at the respective distal ends thereof. The conductor wiring layers 58C to 58F are extended from the bottom plate portion 46A to the other side wall plate portion 46C, with terminal electrodes 60C to 60F formed at the respective distal ends thereof. The conductor wiring layer 58G is extended from the bottom plate portion 46A to the side wall plate portion 46C, with the distal end thereof continuing to a ground electrode 60G that is formed on the projection side portion 46D.

The side wall plate portions 46B and 46C are folded back almost perpendicularly from the base plate portion 46A at the positions of the two-dot chain lines 47A and 47B, whereby the entire circuit board 46 including FPC as described above is formed in nearly a U-shape, and at the position of the two-dot chain line 47C, the projection side portion 46D is folded back almost perpendicularly with respect to the side wall plate portion 46C. The circuit board 46 is inserted in the sleeve 42 in the state of being folded in this way. Reinforcing plates 49A and 49B are affixed to the portions at the distal end side of the side wall plate portions 46B and 46C of the circuit board 46, especially at the portions where the electrodes 60C to 60G are formed, on the surface on the opposite side with respect to the side at which these electrodes are positioned (refer to FIG. 4).

The coaxial cables 32A, 32B, 32C, 32D of the four-core gathered coaxial cable 16 mentioned above are inserted in the sleeve 42, and the conductors of these coaxial cables are electrically connected in a predetermined relationship by soldering or the like to the terminal electrodes 60A to 60F and the ground electrode 60G. One example of that connection relationship is as follows.

The central conductor 34 of the coaxial cable 32A serves as the signal path for the positive analog signal AOP, and the central conductor 34 of the coaxial cable 32B serves as the signal path for the negative analog signal AON, and these central conductors 34 are respectively connected to the terminal electrodes 60A and 60B by solder 62A (in FIG. 4, only the one 32A among the coaxial cables 32A and 32B is shown). Also, the outer conductor 38 of each of the coaxial cables 32A and 32B is at ground potential, and these outer conductors 38 are connected by solder 62B to the ground electrode 60G of the projection side portion 46D. The central conductor 34 of the coaxial cable 32C is the clock signal line (CLK), and the outer conductor 38 of the same coaxial cable 32C is the high potential power supply line (2.8 VDD), and this central conductor 34 and outer conductor 38 are connected to the terminal electrodes 60D and 60C by the solders 62D and 62C, respectively. Moreover, the central conductor 34 of the coaxial cable 32D is the synchronization signal line (HSYNC), and the outer conductor 38 of the same coaxial cable 32D is the low potential power supply line (1.5 VDD), and this central conductor 34 and outer conductor 38 are connected to the terminal electrodes 60C and 60E by the solders 62D and 62C, respectively (in FIG. 4, only the one 32C among the coaxial cables 32C and 32D is shown).

In the structure of the imaging portion of the aforementioned embodiment, the solid state imaging element 44 is driven by the low power supply potential (1.5 VDD) and the high power supply potential (3.3 VDD) being imparted from the external device 24 (refer to FIG. 1) via the coaxial cable 32C, its operation is controlled by the synchronization signal (HSYNC) and the clock signal (CLK) being imparted by the coaxial cable 32D. On the other hand, the image of the observation object region is formed on the light receiving surface of the solid state imaging element 44 via the object lens system 50, converted to an image electrical signal (analog signal) by the solid state imaging element 44, and the positive analog signal (AOP) and the negative analog signal (AON) that correspond to that analog image signal are guided to the external device 24 by the coaxial cables 32A and 32B, and upon undergoing signal processing for converting the analog image signal to a video signal or digital signal, an image is displayed on a display device.

Note that in FIG. 4, the side wall plate portion 46B is shown with dimensions so as not to reach the projection portion 46D, but in some cases, the side wall plate portion 46B may be extended so that the distal end thereof reaches the projection side portion 46D, and the distal end portion of the side wall plate portion 46B may be temporarily joined to the projection side portion 46D by the solder 62B. In this case, it is desirable to also extend the reinforcing plate 49A to the distal end of the side wall plate portion 46B.

While exemplary embodiments of the application have been described and illustrated above, it should be understood that these are exemplary and are not to be considered as limiting. Additions, omissions, substitutions, and other modifications can be made without departing from the spirit or scope of the present application. Accordingly, the application is not to be considered as being limited by the foregoing description, and is only limited by the scope of the appended claims. Suitable modifications can of course be made.

What is claimed is:

1. An imaging part of an electronic visualized catheter, the imaging part comprising:
   an object lens system;
   a solid state imaging element which is positioned to receive light output from the object lens system and which photoelectrically converts the light output from the object lens system into an electric signal, wherein the solid state imaging element has a rectangular shape;

a flexible printed wiring board which is a bent structure having a U-shape; and
a sleeve with a hollow tubular shape comprising a distal end portion which is open, wherein:
an output lens face of the object lens system is planar, and the output lens face is joined to a light receiving surface of the solid state imaging element;
the flexible printed wiring board comprises a bottom plate portion, a first side wall plate portion, and a second side wall plate portion that form the U-shape, wherein the first side wall plate portion and the second side wall plate portion are each a continuous extension of the bottom plate portion, and each extends from the bottom plate portion in a direction away from the distal end portion;
the bottom plate portion comprises an opening that penetrates a plate surface of the bottom plate portion;
the solid state imaging element is disposed on a first surface of the bottom plate portion away from the distal end portion, wherein the first surface faces an inner space surrounded by the bottom plate portion, the first side wall plate portion, and the second side wall plate portion and is joined to a second surface of the solid state imaging element that comprises the light receiving surface,
the first side wall plate portion and the second side wall plate portion are folded along opposite sides of the solid state imaging element, and the light receiving surface of the solid state imaging element faces the distal end portion, and is exposed through the opening in the bottom plate portion;
the output lens face is disposed within the opening in the bottom plate portion;
the object lens system, the solid state imaging element, and the flexible printed wiring board are disposed within the sleeve such that an incident lens face, opposite the output lens face, is positioned at the distal end portion of the sleeve;
the flexible printed wiring board comprises a plurality of conductor wiring layers, wherein the plurality of conductor wiring layers comprise at least one conductor wiring layer which is electrically connected to a terminal portion of the solid state imaging element and extends along the first side wall plate portion;
the plurality of conductor wiring layers further comprise at least one conductor wiring layer which extends along the second side wall plate portion; and
the flexible printed wiring board further comprises a plurality of terminal electrodes positioned to electrically connect to one or more electrical cables which extend to an outside from within the sleeve, and each of the plurality of conductor wiring layers is electrically connected to one of the plurality of terminal electrodes.

2. The imaging part according to claim 1, wherein:
each of the first side wall plate portion and the second side wall plate portion extends in a length direction from the bottom plate portion, and the length direction is parallel to an axial direction of the sleeve.

3. The imaging part according to claim 1, wherein the solid state imaging element is a CMOS image sensor.

4. A catheter comprising:
a feeding tube having an open distal end;
an insertion portion comprising the open distal end of the feeding tube and further comprising an imaging part comprising:
an object lens system;
a solid state imaging element which is positioned to receive light output from the object lens system and which photoelectrically converts the light output from the object lens system into an electrical signal and wherein the solid state imaging element has a rectangular shape;
a flexible printed wiring board which is a bent structure having a U-shape; and
a sleeve with a hollow tubular shape comprising a distal end portion which is open, wherein:
an output lens face of the object lens system is planar, and the output lens face is joined to a light receiving surface of the solid state imaging element;
the flexible printed wiring board comprises a bottom plate portion, a first side wall plate portion, and a second side wall plate portion that form the U-shape, wherein the first side wall plate portion and the second side wall plate portion are each a continuous extension of the bottom plate portion, and each extends from the bottom plate portion in a direction away from the distal end portion;
the bottom plate portion comprises an opening that penetrates a plate surface of the bottom plate portion;
the solid state imaging element is disposed on a first surface of the bottom plate portion away from the distal end portion, wherein the first surface faces an inner space surrounded by the bottom plate portion, the first side wall plate portion, and the second side wall plate portion and is joined to a second surface of the solid state imaging element that comprises the light receiving surface,
the first side wall plate portion and the second side wall plate portion are folded along opposite sides of the solid state imaging element, and the light receiving surface of the solid state imaging element faces the distal end portion, and is exposed through the opening in the bottom plate portion;
the output lens face is disposed within the opening in the bottom plate portion;
the object lens system, the solid state imaging element, and the flexible printed wiring board are disposed within the sleeve such that an incident lens face, opposite the output lens face, is positioned at the distal end portion of the sleeve;
the flexible printed wiring board comprises a plurality of conductor wiring layers, wherein the plurality of conductor wiring layers comprise at least one conductor wiring layer which is electrically connected to a terminal portion of the solid state imaging element and extends along the first side wall plate portion;
the plurality of conductor wiring layers further comprise at least one conductor wiring layer which extends along the second side wall plate portion; and
the flexible printed wiring board further comprises a plurality of terminal electrodes positioned to electrically connect to one or more electrical cables which extend to an outside from within the sleeve, and each of the plurality of conductor wiring layers is electrically connected to one of the plurality of terminal electrodes.

* * * * *